United States Patent [19]
Ristol Debart et al.

[11] Patent Number: 5,846,930
[45] Date of Patent: Dec. 8, 1998

[54] THERAPEUTIC HUMAN ALBUMIN HAVING A LOW ALUMINIUM BINDING CAPACITY

[75] Inventors: Pere Ristol Debart, Sabadell; David Camarero Torrecillas, San Fausto de Camp-Centellas, both of Spain

[73] Assignee: Grupo Grifols, S.A., Barcelona, Spain

[21] Appl. No.: 788,275

[22] Filed: Jan. 24, 1997

[30] Foreign Application Priority Data

Jan. 30, 1996 [ES] Spain ..................... 9600200

[51] Int. Cl.$^6$ ............ A61K 38/16; C07K 13/00
[52] U.S. Cl. ................... 514/2; 514/6; 514/12; 530/362; 530/363; 530/364
[58] Field of Search ................... 530/362, 363, 530/364; 514/2, 6, 12, 21

[56] References Cited

U.S. PATENT DOCUMENTS 4,086,222  4/1978  Lindquist et al. .

FOREIGN PATENT DOCUMENTS 0 452 753 A1  10/1991  European Pat. Off. .
WO 91/00290  1/1991  WIPO .

OTHER PUBLICATIONS

Klein, Gordon L.: *Aluminum in Parenteral Products: Medical Perspective on Large and Small Volume Parenterals.* Journal of Parenteral Science & Technology, 43 (3), 120–124 (1989).

Cuthbertson. B. et al.: *Aluminium and Human Albumin Solutions.* British Medical Journal, 295,1062 (1987).

*Primary Examiner*—Nathan M. Nutter
*Attorney, Agent, or Firm*—Darby & Darby

[57] ABSTRACT

There is described a therapeutic human albumin having a very low capacity for the absorption of aluminium, during storage in a glass receptacle, wherein the final composition of the albumin solution adjusted to be stable and isotonic at a concentration of 5, 20 or 25% of protein in an aqueous medium, preferably, or to any other therapeutic concentration acceptable for intravenous administration, has a citrate content in the final albumin composition equal to or less than 0.5 mM (millimolar) and, preferably, less than 0.037 mM (millimolar).

7 Claims, 1 Drawing Sheet

THERAPEUTIC HUMAN ALBUMIN HAVING A LOW ALUMINIUM BINDING CAPACITY

The present invention relates to a therapeutic human albumin composition having features of a low capacity for the absorption and fixation of multivalent metals leaching from the actual container or receptacle in which the solution is located.

The present invention is used principally in the field of therapeutic plasma proteins for intravenous administration and is especially suitable for albumin solutions although it can be used for other proteins having similar behaviour.

An essential characteristic which any pharmaceutical preparation must have is stability up to its expiration date.

In order to achieve a long stability, possible structural or functional alterations to the active ingredient are determined. Sometimes there is a degradation or alteration in the product which leads to the production of undesirable toxic compounds, the maximum levels of which are laid down by the Pharmacopea or other legal standards.

In the case of plasma proteins for intravenous administration, and in the specific case of some contaminating metals, such as aluminium, the concentration has to be as low as possible, taking into account the toxicity of the product which, in trace form, is capable of producing disorders such as those referred to as senile dementia of the Alzheimer type, dialysis encephalopathy, etc. (Klein, Gordon L.: Aluminum in Parenteral Products: Medical perspective on Large and Small Volume Parenterals. Journal of Parenteral Science & Technology, 43 (3), 120–124 (1989)).

Toxicity studies show that aluminium administered intravenously can accumulate in the tissues and organs (brain), having a toxic effect in patients with renal dysfunction, owing to the deficient elimination thereof.

For this reason, the European health authorities have fixed a level of aluminium in intravenous albumin of less than 200 ppb ($\mu$g/l) in solutions having a protein concentration of 5, 20 or 25%.

Naturally, the maximum limit of the concentration of aluminium in albumin must not only be observed immediately after the preparation of the product but it must also be maintained up to the expiration date.

One of the factors which currently limit the useful life of a therapeutic human albumin is the increase in the concentration of aluminium over the course of time. This increase in aluminium concentration is produced owing to the absorption of said metal from the glass receptacles used to contain the albumin.

It is known that the glass receptacles used as containers for the product contain not negligible amounts of aluminium which can be extracted from the crystal net (Hoiberg, Charles P.: Aluminum in Parenteral Products: Overview of Chemistry Concerns and Regulatory Actions. Journal of Parenteral Science & Technology, 43 (3), 127–131 (1989)).

Commercial vials made of neutral or borosilicate glass (type I) having a low alkaline extractability contain larger amounts of aluminium than does silicate glass with standard surface treatment (ammonium salts or sulphur oxides: glass type II) so that proof of alkalinity is not directly connected with the potential release of aluminium from the glass. It is therefore preferable to use standard commercial glass of type II rather than of type I.

Current technology does not correctly solve the problem of the increase in aluminium during storage, mainly at higher temperatures, these being understood as ambient temperatures of from 25° to 35° C. (Quagliaro, D. A. et al: Aluminum in Albumin for Injection. Journal of Parenteral Science & Technology, 42 (6), 187–190 (1988)).

In order to achieve aluminium levels of less than 200 ppb ($\mu$g/l) in an albumin solution, not only immediately after preparation but also at the end of its shelf life, the albumin is prepared with the avoidance, at all times, of exogenous contamination with aluminium at any stage of the process for fractionating human plasma with ethanol at reduced temperature, or the Cohn method (Cohn, Y. et al. (1946) J. Am. Chem. Soc. 68, 459–475) (use of clarifying filters free from aluminium or having a low aluminium content, filter-aids prewashed in an acid medium, freshly prepared acid or alkaline reagents, . . . ). Using fraction V (according to Cohn's numbering) as the starting material for obtaining albumin, ultrafiltration dialysis techniques were introduced which enable the concentration of aluminium to be reduced to levels of less than 200 ppb ($\mu$g/l). These procedures were first introduced in 1987 by the Scottish National Blood Transfusion Service (McBay, W. E. et al.: Aluminium and human albumin solutions. British Medical Journal, 295, 1062 (1987)), then by the Millipore company in collaboration with the Swiss Red Cross (internal communication) and a similar method was later described by Kabi (patent application WO 91/00290).

These procedures were based on washing polyvalent metals from the albumin by ionic displacement with monovalent metals, during dialysis operations. Thus, the amount of a metal ion, such as aluminium, is reduced by diafiltration with retaining membranes of 10 kD or 30 kD, which retain the proteins (having a higher molecular weight) and permit the sieving of ions or molecules that are smaller than the membrane pores.

This washing operation cannot be readily carried out unless the concentration of monovalent ions (for example: sodium chloride) is increased, which permits the displacement of polyvalent metals, such as aluminium. One method of maintaining the concentration of monovalent ions (for example, sodium chloride) at a constant level is to use the known technique of diafiltration at constant volume. The current techniques for the diafiltration of albumin were introduced with the aim of reducing the aluminium (and other metals) to values of less than 200 ppb, and also with the aim of reducing the ethanol and the excess salts (sodium chloride; or other free low-molecular-weight compounds) which may be present in fraction V of Cohn's fractionation method, which fraction is used as the starting material. In this manner, it is feasible to reduce the aluminium ions to less than 200 ppb and even to a value of less than 50 ppb, using three volumes of a dialysis solution formed by a salt having monovalent ions (sodium chloride).

However, the solutions so obtained, having a level less than 200 ppb ($\mu$g/l), stored in their final container (of type I or type II glass) and stored (stability assay) at room temperature (25°–35° C.), gradually increase their aluminium level over time, so that they easily exceed the established limits of 200 ppm ($\mu$g/l) at the expiration date (3 years, for example).

Therefore, it still remains to find a technical solution to this phenomenon of an increase in aluminium during the period of preservation or storage of protein solutions, mainly of albumin, in their glass containers.

The object of the present invention was therefore to provide an albumin preparation having a low aluminium binding capacity, which can be stored at higher than usual temperatures (room temperature or higher) or else that its shelf life or expiration date can be prolonged.

Prior to the present invention, it was generally believed that the release of aluminium from the (glass) container was due exclusively to the albumin's capacity to fix and transport metals, and that therefore it was not possible to solve this problem unless the composition or surface of the glass used were changed (preparation of non-standard special glasses).

Figure 1:
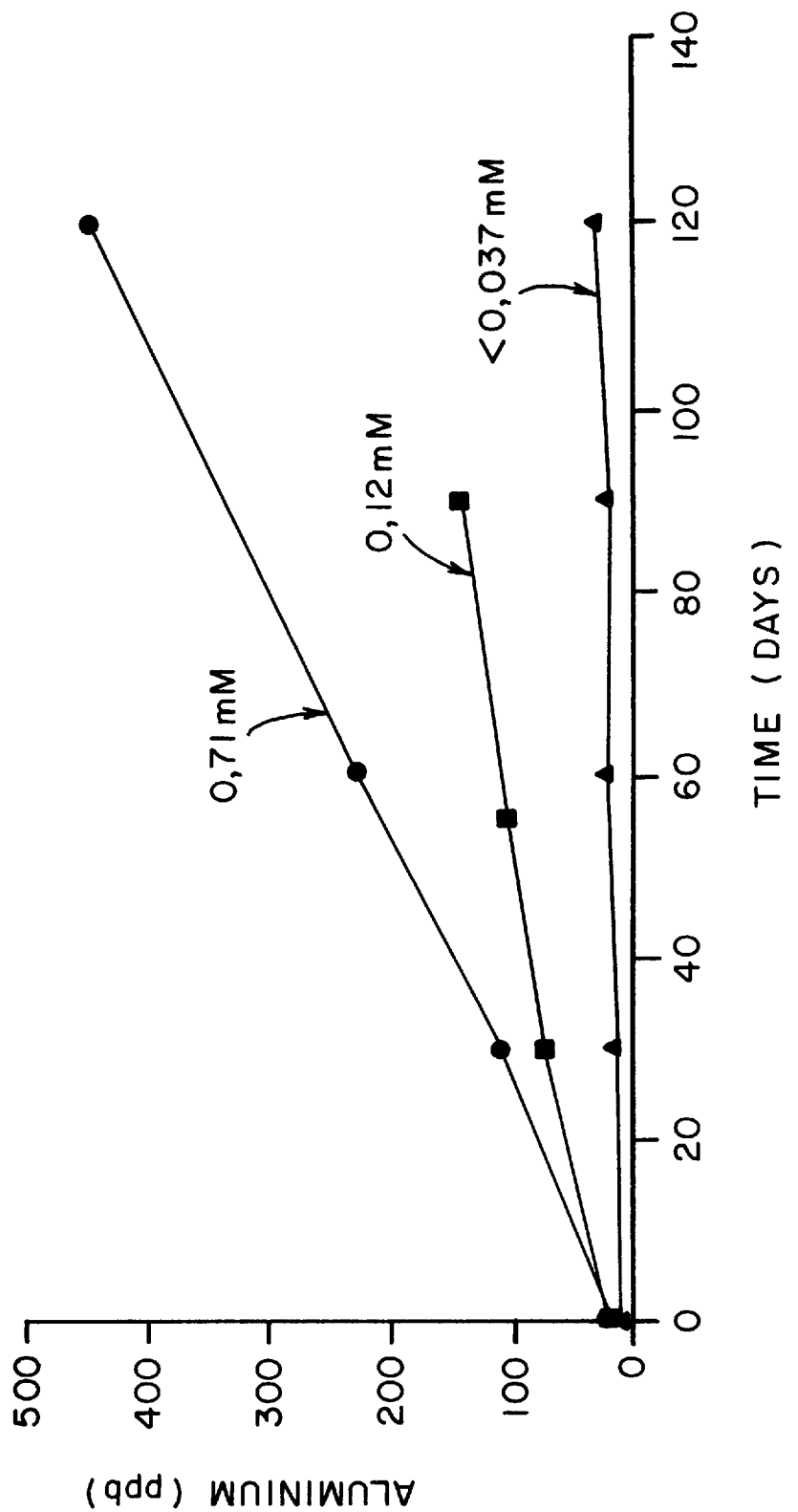
FIG. 1 is a graph showing the amount of aluminum in therapeutic albumin solutions stored in glass vials over time and in the presence of varying amounts of citrate.

Investigations carried out by the inventors have allowed to demonstrate the causal nature of the phenomenon of the increase in aluminium during the storage of albumin in vials and have made it possible to develop a final formula for a human therapeutic albumin which overcomes the mentioned disadvantages.

Fresh or recovered human plasma from which therapeutic albumin is prepared contains an anticoagulant solution in the formula of which the citrate ion is always present.

On studying the distribution of the citrate within the plasma fractions, the presence of substantial quantities of that anion is observed in fraction V which is used as the starting material for the preparation of albumin (approximately from 10 to 20% relative to the initial citrate content in the plasma, depending on the system used for the separation of fraction V).

This citrate contamination occurs in all the albumin solutions prepared by Cohn's method and the usual concentration exceeds the value of 1 mmol/liter in the final composition of the end product (for example with 20% of proteins) despite the fact that the solution of the starting fraction V is diafiltered to eliminate the aluminium to the extent of values of less than 200 ppb and even 50 ppb or less.

The inventors have discovered that the presence of citrate (always present in fraction V used as the starting material) in albumin solutions stored in glass greatly accelerates the release of aluminium from the glass receptacles containing the solutions. This effect has been demonstrated experimentally, showing a logarithmic response between the rate of release and the concentration of citrate. Therefore, the citrate should be lowered to levels lower than the values occurring in fraction V.

The release mechanism, although not well known at present, is assumed to be based on an equilibrium between the albumin-citrate complex, the dissociation of which by means of an ionic charge promotes the presence of free citrate which is capable of causing aluminium to migrate from the glass. In the absence of a free citrate anion, the albumin cannot capture aluminium by itself although it is nonetheless a good carrier and can strongly associate with any polyvalent metal.

As the outcome of their investigations, the inventors have discovered that significant reductions in the increase of aluminium can be obtained when the final composition of the albumin solution is adjusted to be stable and isotonic at a concentration of 5, 20 or 25% of protein in an aqueous medium, preferably, or to any other therapeutic concentration acceptable for intravenous administration, and is introduced into containers (vials) of standard commercial glass (type II), preferably, and when the content of citrates in the final albumin composition is equal to or less than 0.5 mM (millimolar) and, preferably, less than 0.037 mM (millimolar).

The product obtained satisfies specifications and European regulations, being less than 200 ppb ($\mu$g/l) of aluminium and generally <50 ppb ($\mu$g/l) of aluminum. Thus, the product obtained is stable for more than 3 years at a temperature of 25±10 C., without exceeding the limits established in respect of the maximum content of aluminium under storage conditions.

The invention will be explained hereinafter on the basis of non-limiting examples for carrying out the invention.

EXAMPLE 1

Three groups of fresh frozen plasma containing ACD (citric/dextrose) as anti-coagulant were fractionated by Cohn's method until fraction V was obtained. After diafiltration and adjustment to a 20% protein concentration in the adjusted sterile bulk, each group was filled under aseptic conditions into 50 ml vials (neck 20 mm in diameter) of standard type II glass (company BSN), and were sealed hermetically. They were subsequently subjected to pasteurisation (10 hours at 60 C.) and accelerated quarantine (14 days at 31 C.).

The citrate concentration of each batch was then determined and a test was carried out in respect of the accelerated release of aluminium into the 20% packed albumin when submitting it to 45 C., the aluminium content being determined in each case after different exposure times.

The results obtained are indicated in Table 1 and are shown graphically in FIG. 1 which correlates the aluminium content on the ordinate with the exposure time, at each of the citrate concentrations obtained.

TABLE 1

Relationship between the final citrate concentration and the accelerated release of aluminium over over the storage time at 45° C.

| CITRATE CONCENTRA-TION | | ALUMINIUM CONCENTRATION (ppb) (Exposure time 45° C.: days) | | | | LINEAR REGRESSION (CORRELA- |
|---|---|---|---|---|---|---|
| (g/l) | (mM) | t = 0 | t = 30 | t = 60 | t = 120 | TION) |
| 0.21 | 0.71 | 20.05 | 110.3 | 227.35 | 446 | 3.5906xt + 12.42 (r = 0.9992) |
| 0.036 | 0.12 | 24.35 | 75.48 | 104.25 | — | 1.2806xt + 30.26 (r = 0.9922) |
| <0.011 | 0.037 | 12.13 | 12.40 | 20.43 | 30.60 | 0.1442xt + 10.20 (r = 0.8941) |

It should be noted that, although the initial aluminium content (t=0) is of the same order and very low in all three cases (less than 25 ppb), the same does not apply to the citrate concentration which appears to be directly responsible for the increase in aluminium over the exposure time at elevated temperature (45 C.).

The linear correlations are significant in all cases (principally those which contain 0.71 and 0.12 mM of citrate) and therefore the different slopes of the aluminium release speed are also significant.

The different aluminium release speeds of 3.5906 and 0.1422 ppb/day obtained as a result of the presence of 0.71 or <0.037 mM, respectively, of citrate in the albumin stand out, indicating that the release rate is 3.5906/0.1422=25 fold between the release speeds obtained with the two citrate concentrations.

EXAMPLE 2

Various batches of final albumin adjusted by stabilisers (sodium caprylate and sodium tryptophanate) and isotony (sodium chloride) to a neutral pH were sterilised by filtration.

Each solution was filled under aseptic conditions in two equal parts into 50 ml vials (neck 20 mm in diameter), some of which were of standard commercial type II glass (company BSN) and others of which had undergone special surface treatment (metabisulphite). The citrate and aluminium content of the vials was determined, showing that, in the final formulation of the albumin of the 3 batches processed, the citrate content was less than the quantification limit of the technique (<0.011 g/l or <0.037 mM). These batches underwent accelerated aluminium release at 45 C. Samples were taken from each of the batches to determine the release of aluminium over time.

The results are indicated in the following Table 2:

TABLE 2

Accelerated release (45° C.) of aluminium albumin with respect to the glass of the vial

| GLASS VIAL | CITRATE CONCENTRATION | | ALUMINIUM CONCENTRATION (ppb) (Exposure time 45° C.: days) | | | | | LINEAR CORRELATION |
|---|---|---|---|---|---|---|---|---|
| | (g/l) | (m/M) | t = 0 | t = 30 | t = 60 | t = 90 | t = 120 | |
| Metabisulphite (special) | <0.011 | <0.037 | 12.13 | 10.73 (±5.09) | 17.43 (±0.60) | 13.00 (±2.75) | 26.13 (±2.04) | 0.1009xt + 9.83 (r = 0.7655) |
| Type II (BSN) | <0.011 | <0.037 | 12.13 | 12.40 (±4.24) | 20.43 (±7.33) | 18.13 (±4.79) | 30.60 (±3.83) | 0.1422xt + 10.20 (r = 0.8941) |

Taking into account the linear correlations obtained in the aluminium release kinetics, with the two groups of vials which had undergone different surface treatment of the glass, and the small difference between the slopes of the curves or release speed, the conclusion reached is that the type of glass is not a determining factor in the rate of release of aluminium, provided that the citrate is present at a sufficiently reduced level (close to the limit of detection of the technique <0.011 g/l).

EXAMPLE 3

The same final albumin solution stabilised with sodium caprylate and sodium tryptophanate at 0.016M in each case, and at a 20% protein concentration, and containing 0.15M sodium chloride and adjusted to pH 7.0±0.2, was sterilised by filtration using a 0.22 μm membrane.

The solutions were filled into 50 ml type II glass vials to which known quantities of sodium citrate were added and pasteurisation was carried out for 10 hours at 60 C. The solutions underwent an accelerated aluminium release by being stored at 45 C.

At the times indicated in Table 3, samples were taken to determine the aluminium content.

TABLE 3

Acceleration of release of aluminium (at 45° C.) in 20% albumin with respect to the concentration of citrate

| CITRATE CONCENTRATION | | ALUMINIUM CONCENTRATION (ppb) (Exposure time 45° C.: days) | | | | |
|---|---|---|---|---|---|---|
| (g/l) | (mM) | t = 0 | t = 30 | t = 60 | t = 90 | t = 150 |
| <0.011 | <0.037 | 9.0 | 10.0 | 28.2 | 31.0 | 43.6 |
| 6.12 | 1.8 | 164.2 | 204.6 | 330.2 | — | 721.6 |

TABLE 3-continued

Acceleration of release of aluminium (at 45° C.) in 20% albumin with respect to the concentration of citrate

| CITRATE CONCENTRATION | | ALUMINIUM CONCENTRATION (ppb) (Exposure time 45° C.: days) | | | | |
|---|---|---|---|---|---|---|
| (g/l) | (mM) | t = 0 | t = 30 | t = 60 | t = 90 | t = 150 |
| 9.51 | 2.8 | 161.4 | 240.6 | 349 | — | 886.4 |
| 23.1 | 6.8 | 165.6 | 287.2 | 418.8 | — | 913.6 |
| 40.1 | 11.8 | 177.2 | 276.3 | 585 | — | 1.176.0 |

This clearly shows the effect of the deliberately added citrate on the accelerated release of aluminium, for the same batch of albumin and glass container. Likewise, the table demonstrates a notable difference in the final aluminium level after 150 days at 45 C. between the solutions with albumin at <0.037 mM and 1.8 mM of citrate, corresponding to 43.6 and 721.6 ppb of aluminium, respectively. Therefore, a small degree of contamination with citrate or a citrate residue greatly accelerates the release of aluminium.

We claim:

1. A therapeutic package comprising a glass container for sterile solutions containing therein an aqueous human albumin composition which comprises human albumin at a concentration acceptable for intravenous administration, wherein said composition comprises less than 0.12 millimolar citrate, wherein said human albumin composition attains a concentration of aluminum of not greater than 100 parts per billion after storage at 45° C. for thirty days in said glass container.

2. The therapeutic package of claim 1 wherein said human albumin is at a concentration of from between 5 and 25 percent.

3. The package of claim 2 wherein said albumin composition comprises albumin-stabilizing compounds.

4. The package of claim 2 wherein said albumin composition is an isotonic solution.

5. The package of claim 1 wherein said albumin composition comprises less than 0.037 millimolar citrate.

6. The package of claim 3 wherein said wherein said stabilizing compounds are selected from the group consisting of sodium caprylate, sodium tryptophanate, and combinations thereof.

7. The package of claim 4 wherein said albumin composition comprises sodium chloride.

* * * * *